(12) United States Patent
Veneman et al.

(10) Patent No.: US 11,339,116 B2
(45) Date of Patent: May 24, 2022

(54) REACTIVE SEPARATION PROCESS TO CONVERT CYCLIC ALKYLENE UREAS INTO THEIR CORRESPONDING ALKYLENE AMINES

(71) Applicant: NOURYON CHEMICALS INTERNATIONAL B.V., Arnhem (NL)

(72) Inventors: Rens Veneman, Amersfoort (NL); Antoon Jacob Berend Ten Kate, Arhem (NL); Karl Fredrik Lake, Södertälje (SE); Eike Nicolas Kantzer, Uddevalla (SE); Slavisa Jovic, Utrecht (NL); Rolf Krister Edvinsson, Partille (SE); Ina Ehlers, Ödsmål (SE); Hendrik Van Dam, Ede (NL); Michiel Jozef Thomas Raaijmakers, Deventer (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,377

(22) PCT Filed: Aug. 7, 2018

(86) PCT No.: PCT/EP2018/071318
§ 371 (c)(1),
(2) Date: Feb. 11, 2020

(87) PCT Pub. No.: WO2019/030189
PCT Pub. Date: Feb. 14, 2019

(65) Prior Publication Data
US 2020/0361851 A1    Nov. 19, 2020

(30) Foreign Application Priority Data

Aug. 11, 2017  (EP) .................................. 17185943

(51) Int. Cl.
*C07C 209/68* (2006.01)
*C07C 209/86* (2006.01)

(52) U.S. Cl.
CPC .......... *C07C 209/68* (2013.01); *C07C 209/86* (2013.01)

(58) Field of Classification Search
None
See application file for complete search history.

(56) References Cited

U.S. PATENT DOCUMENTS 2,514,380 A    7/1950  Duschinsky
2,812,333 A    11/1957 Steele

OTHER PUBLICATIONS

EPO, European Extended Search Report issued in European Application No. 17185943.2, dated Feb. 19, 2018.
EPO, International Search Report and Written Opinion issued in International Application No. PCT/EP2018/071318, dated Oct. 11, 2018.

*Primary Examiner* — Sudhakar Katakam
*Assistant Examiner* — Jennifer C Sawyer
(74) *Attorney, Agent, or Firm* — Lorenz & Kopf, LLP

(57) ABSTRACT

A process to convert cyclic alkylene ureas into their corresponding alkylene amines is provided. An exemplary process includes reacting the cyclic alkylene ureas with an amine compound chosen from the group of primary amines or secondary amines that have a higher boiling point than the alkylene amines formed during the process, wherein the process is a reactive separation process and the reaction mixture contains less than about 10 wt % of water on the basis of total weight of the reaction mixture.

20 Claims, 2 Drawing Sheets

Chemical structures
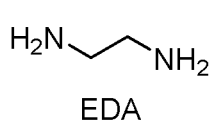
EDA
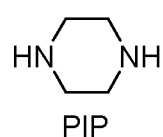
PIP
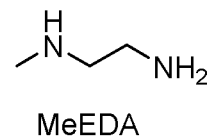
MeEDA
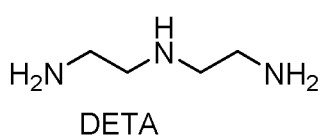
DETA
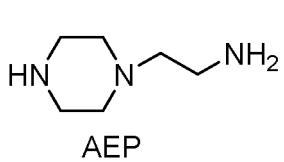
AEP
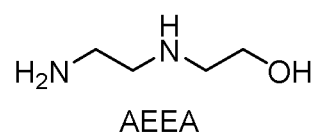
AEEA
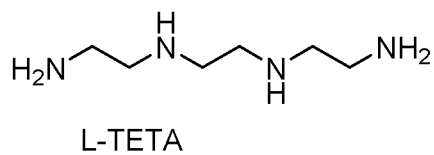
L-TETA
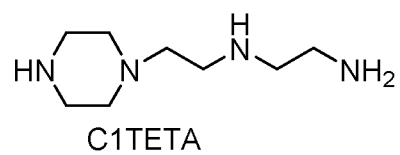
C1TETA
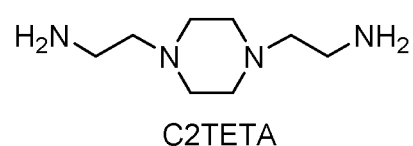
C2TETA
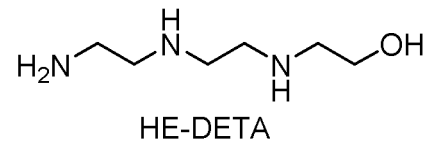
HE-DETA
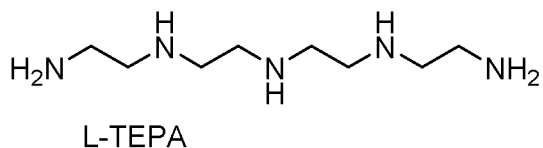
L-TEPA
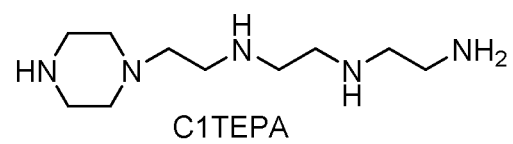
C1TEPA
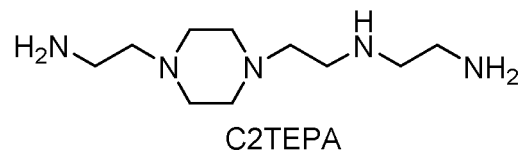
C2TEPA
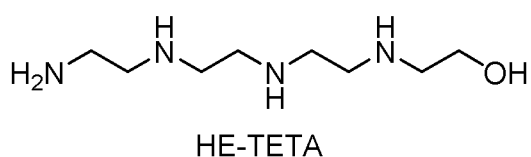
HE-TETA

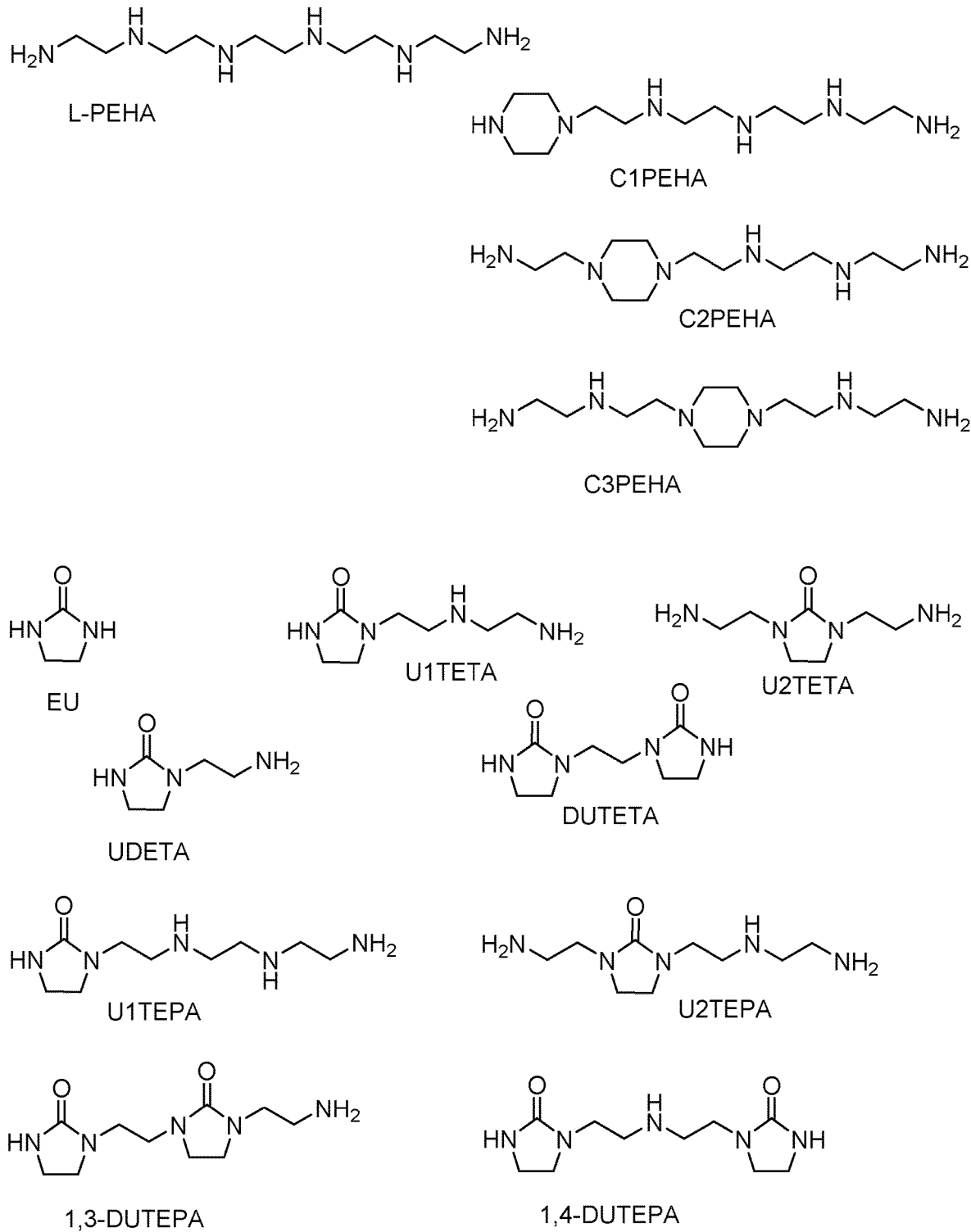

REACTIVE SEPARATION PROCESS TO CONVERT CYCLIC ALKYLENE UREAS INTO THEIR CORRESPONDING ALKYLENE AMINES

CROSS-REFERENCE TO RELATED APPLICATION

This application is a U.S. National-Stage entry under 35 U.S.C. § 371 based on International Application No. PCT/EP2018/071318, filed Aug. 7, 2018, which was published under PCT Article 21(2) and which claims priority to European Application No. 17185943.2, filed Aug. 11, 2017, which are all hereby incorporated in their entirety by reference.

TECHNICAL FIELD

The present invention relates to a reactive separation process to convert cyclic alkylene ureas into their corresponding alkylene amines

BACKGROUND

Two adjacent nitrogen atoms linked by one alkylene unit and one carbonyl moiety form a cyclic alkylene urea. When alkylene is ethylene, an ethylene amine (EA) in which two nitrogen atoms are linked intramolecular by a carbonyl moiety

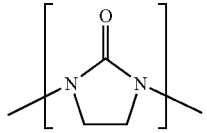

is here referred to as an UEA. Replacing the carbonyl bridge with two hydrogen atoms yields the corresponding ethylene amine. For example: EU↔EDA, UDETA↔DETA, UAEEA↔AEEA, UTETA↔L-TETA, UTEPA↔TEPA. Some higher amines host more than one carbonyl moiety, e.g. DUTETA the diurea of L-TETA. The carbonyl moiety may link nitrogen atoms on two separate molecules. For example H$_2$NC$_2$H$_4$NH—CO—NHC$_2$H$_4$NH$_2$ and replacing the carbonyl moiety with two hydrogen atoms here yields two EDA. As to naming of the molecules, EDA stands for ethylene diamine, DETA for diethylene triamine, L-TETA for linear triethylene tetraamine, L-TEPA for linear tetraethylene pentamine, L-PEHA for linear pentaethylene hexamine, AEEA stands for aminoethylethanolamine. When there is a single cyclic urea in the molecule this is indicated by adding a U in front of the name, e.g. UTETA means the cyclic urea of L-TETA, while when there are two cyclic ureas in the molecule this is indicated by DU, i.e. DUTETA means the internal cyclic diurea of L-TETA. If there is a number indicated for the U this refers to the amino group where the U group is located (starting from the terminal amine unit of the alkylene amine chain). U1TETA is the monocyclic urea of L-TETA wherein the urea is between the first (terminal) and the second amine unit, U2-TETA is the monocyclic urea of L-TETA wherein the urea is between the second and third amine group in the TETA molecule (i.e. an internal cyclic urea is formed). DUTETA or DU1,3TETA is the dicyclic urea of L-TETA, the cyclic urea units inherently being between the first and second amine group, and the third and fourth amine group, respectively. DUTEPA exists in two versions DU1,3-TEPA and DU1,4-TEPA. There is one exception to this naming and that is that instead of UEDA the abbreviation EU is used, which stands for ethyleneurea. It is possible that between two amine groups in an alkylene amine two alkylene groups are present, resulting in a so-called cyclic unit (when having two ethylenes this cyclic unit is called a piperazine unit). This is indicated by adding a C in front of the name, e.g. CTETA means L-TETA wherein one unit —HN—C2H4-NH— is present as

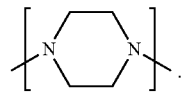

If there is a number indicated with the C this refers to the amino group where the cyclic group is located. As an example N-[(2-aminoethyl)2-aminoethyl]piperazine is in this document referred to as C1-TETA.

U.S. Pat. No. 2,514,380 discloses cyclic urea compounds and their hydrolysis into diamines. This hydrolysis is said to be done under acidic or alkaline conditions. In the Examples a process involving refluxing with either concentrated aqueous HCl or concentrated aqueous NaOH is employed.

U.S. Pat. No. 2,812,333 discloses a process to prepare the cyclic urea 1-(2-hydroxyethyl)imidazolidone-2 (which corresponds to the cyclic urea of AEEA). The carbonyl unit in the cyclic urea is said to be removed by reaction with water, which in one of the examples is done by heating a 12 wt % solution of the compound to 175° C., resulting in a very limited amount of the compound being converted per hour.

The process of the present invention as indicated is about converting cyclic alkylene ureas into their corresponding alkylene amines, more in particular it is about removing the carbonyl group of a cyclic alkylene urea to give the corresponding alkylene amine according to the following general reaction scheme:

Pending application PCT/EP2017/052944 relates to a process to convert cyclic alkylene ureas into their corresponding alkylene amines wherein the process is performed by reaction with an amine compound and wherein the amine compound is a primary amine, a cyclic secondary amine or a bicyclic tertiary amine.

It was now found that amines are effective in converting cyclic alkylene ureas into their corresponding (linear) alkylene amines with very high efficiency if a reactive separation process is used under the right conditions.

Accordingly, the present invention now provides a process to convert cyclic alkylene ureas into their corresponding alkylene amines by reaction with an amine compound chosen from the group of primary amines, or secondary amines that have a higher boiling point than the alkylene amines formed during the process, wherein the process is a reactive separation process and the reaction mixture contains less than 10 wt % of water on the basis of total weight of the reaction mixture.

BRIEF SUMMARY

A process to convert a cyclic alkylene urea into a corresponding alkylene amines, the process is provided. An exemplary process includes reacting the cyclic alkylene ureas with an amine compound chosen from the group of primary amines or secondary amines that have a higher boiling point than the alkylene amines formed during the process, wherein the process is a reactive separation process and the reaction mixture contains less than about 10 wt % of water on the basis of total weight of the reaction mixture.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

Unexpectedly, when using the process of the present invention alkylene amine product is with high efficiency formed and simultaneously separated from the reaction mixture in a good yield using relatively mild conditions. The urea free compounds can be prepared and isolated as one fraction at relatively low temperatures, especially urea free compounds that are relatively volatile. Because amines are used to convert cyclic alkylene ureas into their corresponding alkylene amines, degradation of the alkylene amines is to a large extent avoided, like might occur during treatment with strong bases like NaOH or strong acids like HCl. The process of the present invention has as a further advantage that water or any other adjuvant need not be added and that the respectively obtained cyclic alkylene urea and cyclic alkylene carbamate can be also recovered as products.

Examples of reactive separation processes are process driven by volatility differences such as for example reactive flashing, membrane distillation, membrane evaporation, stripping or reactive distillation, whereby reactive distillation is preferred.

The process of the invention can for many embodiments be represented by the following reaction: UEA1+EA2→EA1↑+UEA2 wherein UEA1 is the cyclic alkylene urea, EA2 the amine compound, and the up-arrow indicates that the formed alkylene amine EA1 is separated from the reaction mixture, and wherein EA2 has a higher boiling point than EA1

In a preferred embodiment of the process the reaction mixture contains less than 7 wt %, even more preferred less than 5 wt % of water on the basis of total weight of the reaction mixture. In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

In another preferred embodiment wherein more than the required amount of water is present in a composition of cyclic alkylene ureas and optionally the amine compound, it is preferred to first perform a step wherein excess of water is removed. Such a step may involve a water evaporation, flashing, stripping, extraction, adsorption or other physical step as well as chemical water scavenging techniques known to the person skilled in the art, preferably by a distillation step.

The process may be conducted at any suitable pressure. During the reaction, the pressure in the reactive separation system is preferably at most 127 bara, more preferably at most 50 bara, and yet even more preferably at most 25 bara. The larger the alkylene amine produced is, the more preferable an even lower pressure is. Such as for example if the urea to be converted is a diethylene triamine based one, the pressure is preferably less than 15 bar if the urea to be converted is a triethylene tetramine based one the pressure is preferably less than 5 bar. Hence in embodiments the process is performed at even lower pressures, such as less than 15 bar or even more preferably lower pressure, such as less than 5 bar.

In another preferred embodiment the process is done below atmospheric pressure, such as less than 700 mbar, more preferably below 100 mbara, even more preferably below 25 mbara, and most preferably below 5 mbara.

The pressure is preferably at least 0.1 mbara.

The process of the invention is preferably done at a temperature of at least 150 C, preferably at least 200 C, more preferably at least 230° C., and most preferably of at least 250 C. Preferably, the temperature during the process does not exceed 400° C., more preferably 350 C.

A person skilled in the art will be capable of optimizing the conditions, i.e. temperature, pressure and auxiliary compounds such as stripping gases, dependent on the ethylene amines to be separated.

The process of the present invention in embodiments is performed for a time of between 1 minute and 12 hours. Preferably the reactive separation is run in less than 10 hours, more preferably in less than 8 hours, most preferably less than 5 hours.

In a preferred embodiment in the process of the invention the cyclic alkylene urea (corresponding with UEA1 in above schematic reaction) that is subjected to the conversion to give a corresponding alkylene amine (EA1) are:

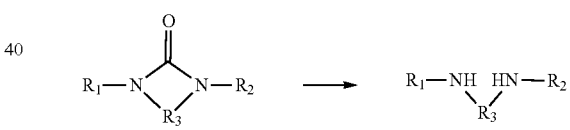

Wherein R1 and R2 each independently are chosen from the group of hydrogen, an alkylene amine group of the formula X—R3-(NH—R3-)p-, or an alkoxy group of formula X—R3-(O—R3-)n-, or a group combining such alkylene amine and alkoxy units p and n, wherein one or more units ~N—R3-N~ may be present as either one of the rings

and wherein each R3 independently is as defined below and X may be hydroxyl, amine, a linear or branched C1-C20 hydroxyalkyl or C1-C20 aminoalkyl group, n and p independently is at least 0, preferably at least 1, more preferably 2-20, optionally containing one or more piperazine, or alkylene urea groups, or when p or n is 0 may be a C1-C20 hydroxyalkyl or C1-C20 aminoalkyl, and R3 is alkylene or substituted alkylene.

In a preferred embodiment R2 is a hydrogen atom and R1 is not a hydrogen atom.

In a more preferred embodiment R2 is a hydrogen atom and R1 may contain a repeating alkylene amine group, even more preferably a repeating ethylene amine group of the formula X—(NH—C2H4)n wherein optionally one or more units —NH—C2H4-NH— may be present as one of the rings

and wherein n is 1 to 20, and X may be a hydrogen atom, an aminoalkyl, an hydroxyalkyl, N-imidazolidinonealkyl or piperazinoalkyl group, most preferably wherein the alkyl is ethyl.

R3 is preferably ethylene or propylene, optionally substituted with C1-C3 alkyl substituents, such as most prominently can be a monomethyl ethylene. More preferably it is an unsubstituted ethylene or propylene, most preferably ethylene.

Some examples of cyclic alkylene ureas (hereinabove in embodiments also referred to as UEA1's) that are most preferred are EU (ethyleneurea), UDETA (the urea of diethylene triamine), UTETA (the ureas of triethylene tetraamine, i.e. U1TETA or U2TETA, dependent on whether the urea is between the 1st and 2nd amine in the chain or 2nd and 3rd amine, respectively), DUTETA (the diurea of triethylene tetramine), UTEPA (the ureas of tetraethylene pentamine, i.e. U1TEPA, U2TEPA depending on where the urea unit is located), DUTEPA (DU1,3TEPA, DU1,4TEPA, the diureas of tetraethylene pentamine), UAEEA (the urea of aminoethylethanolamine), HE-UDETA (the urea of hydroxyethyl diethylene triamine, that can exist in two isomers HE-U1DETA and HE-U2DETA), HE-UTETA (the urea of hydroxyethyl triethylene tetraamine, that can exist in three isomers HE-U1TETA, HE-U2TETA and HE-U3TETA), HE-DUTETA (the diurea of hydroxyethyl triethylene tetraamine), or any mixture of these. The molecular structures of a number of the above cyclic alkylene ureas are given in FIG. 1. To avoid any confusion, if a number is given for the amine group where the cyclic urea unit U is located, the amine groups are counted from the terminal amine group on the molecule which in the case of hydroxyethylated ethylene amines is the amine group at the end not containing the hydroxyl group.

The amine compound (hereinabove in embodiments also referred to as EA2's) can be a primary amine or secondary amine. Primary amines are amine functional compounds in which the amine group is of the formula R4-NH2 and wherein R4 can be any organic group, preferably an aliphatic hydrocarbon with optional heteroatoms such as oxygen and/or nitrogen. Secondary amines are amines of the formula R5-NH—R6, wherein R5 and R6 can be any organic group, preferably an aliphatic hydrocarbon with optional heteroatoms such as oxygen and/or nitrogen. Secondary amines can be either linear or cyclic. On all the above groups R4 to R6 substituents can be present, like alkyl, aminoalkyl, or hydroxyalkyl groups.

In this document a compound is defined as a primary amine or a secondary amine if one of the amine groups in the compound is a primary amine or secondary amine, independent of if this compound contains further amine groups that may be different in their nature. A compound can also contain two or more different amine functionalities, e.g. a primary amine and a secondary amine functionality, and also contain more than one of each.

Preferred examples of primary amines are alkylamines, linear ethylene amines, and alkanolamines. Structures of some of the amine compounds are given in FIG. 1

The amine compound is preferably a compound with more than one amine group wherein at least one of the amine groups is a primary amine, even more preferably it is an amine wherein two amine groups are a primary amine, or wherein one amine is a primary amine group and that in addition contains a hydroxyl group. The amine compound is preferably a compound different than R1-NH—R3-NH—R2 that is obtained by the process of the invention.

In another preferred embodiment the amine compound is a compound that can bind with the carbonyl group from the cyclic alkylene urea (UEA). Preferred amine compounds include an alkylene amine, optionally containing a piperazine unit in their structure, or an alkanol amine compound, optionally containing a piperazine unit in their structure, even more preferably an amine compound that binds the carbonyl group from the cyclic alkylene urea to give among others another linear or cyclic alkylene urea or linear or cyclic alkylene carbamate, that is larger or less volatile than the alkylene amine formed by the process of the invention. Alkylene amines, possibly partially converted into their cyclic alkylene urea counterparts are preferred over alkanolamines (and over alkanolamine counterparts wherein a conversion to a carbamate or urea of these alkanolamines found place)

The amine compounds that are preferably used are in embodiments ethylenediamine (EDA), N-methylethylenediamine (MeEDA), diethylene triamine (DETA), ethanolamine (MEA), aminoethylethanolamine (AEEA), HE-DETA, HE-TETA, HE-UTETA, linear triethylene tetramine (L-TETA), N-diethyldiamine-2-imidazolidinone (U1TETA), N,N'-diaminoethyl-2-imidazolidinone (U2TETA), linear tetraethylene pentamine (L-TEPA), pentaethylene hexamine (PEHA), and the mono cyclic ureas of TEPA and PEHA (i.e. U1TEPA, U2TEPA, U1PEHA, U2PEHA, U3PEHA), the dicyclic urea isomers of PEHA (i.e. DUPEHA), and the C1, C2, C3 analogues of alkylene amines such as C1TETA (N1-(2-(piperazin-1-yl)ethyl)ethane-1,2-diamine), C1TEPA (N1-(2-aminoethyl)-N2-(2-(piperazin-1-yl)ethyl)ethane-1,2-diamine), C2TEPA (N1-(2-(4-(2-aminoethyl)piperazin-1-yl)ethyl)ethane-1,2-diamine), C1PEHA (N1-(2-aminoethyl)-N2-(2-((2-(piperazin-1-yl)ethyl)amino)ethyl)ethane-1,2-diamine), C2PEHA (N1-(2-aminoethyl)-N2-(2-(4-(2-aminoethyl)piperazin-1-yl)ethyl)ethane-1,2-diamine) and C3-PEHA (N1,N1'-(piperazine-1,4-diylbis(ethane-2,1-diyl))bis(ethane-1,2-diamine).

More preferred combinations of cyclic alkylene ureas and amine compounds are in below Table 1

TABLE 1

| Cyclic alkylene urea | The amine compound |
|---|---|
| EU | DETA, TETA, TEPA, PEHA, AEEA, HE-DETA, HE-TETA, UTETA, UTEPA, UPEHA, HE-UTETA, |
| UDETA | TETA, TEPA, PEHA, AEEA, HE-DETA, HE-TETA, UTETA, UTEPA, UPEHA, HE-UTETA |
| UAEEA | TETA, TEPA, PEHA, HE-DETA, HE-TETA, UTETA, UTEPA, UPEHA, HE-UTETA, |

TABLE 1-continued

| Cyclic alkylene urea | The amine compound |
|---|---|
| UTETA, or DUTETA | TEPA, PEHA, HE-DETA, HE-TETA, UTETA, UTEPA, UPEHA, or HE-UTETA |
| HE-UDETA | TEPA, PEHA, HE-TETA, UTEPA, UPEHA, or HE-UTETA |
| UTEPA or DUTEPA | PEHA,, HE-TETA, UTEPA, UPEHA, or HE-UTETA |
| UPEHA, DUPEHA or TUPEHA | UPEHA, or HE-UTETA |

For the above molecules the position of the U is not mentioned, as it can be at any place in the molecule, i.e. UTETA can be U1TETA or U2TETA EDA stands for ethylene diamine, DETA for diethylene triamine, TETA for triethylene tetramine, TEPA for tetraethylene pentamine, PEHA for pentaethylene hexamine, and, EU, UDETA, UTETA, UTEPA, and UPEHA for their respective monoureas. DUTETA, DUTEPA, and DUPEHA stands for the diureas of TETA, TEPA and PEHA. TUPEHA stands for the triurea of PEHA. AEEA for aminoethylethanolamine, HE stands for the presence of a hydroxyethyl group at one of the terminal amines of the mentioned ethylene amine It should be understood that the process of the invention can also be employed for reaction mixtures that contain two or more amine compounds and/or cyclic urea compounds.

It is possible to carry out the process of the invention in a single step. However, if the starting material contains a number of different alkylene ureas that are converted into alkylene amines with varying boiling ranges, it may be attractive to carry out the conversion in at least two stages, wherein the boiling point of the alkylene amines separated increases with the stage. That is, the alkylene amines removed in the first stage have a boiling point which is below that of at least some of the alkylene amines removed in the second stage, which in turn is lower than the boiling point of the alkylene ureas removed in the third stage, if present, and so on.

For example, in a first step, EU may react with a higher boiling amine compound to form EDA, which is removed by distillation, and a cyclic alkylene urea, and in a second step, UDETA may react with a higher-boiling amine compound to form DETA, which can be removed by distillation, and a cyclic alkylene urea.

In another preferred embodiment the amine compound is present during the process in a molar amount of between 0.15 and 25 equivalent based on the total molar amount of cyclic alkylene urea.

In an embodiment in a subsequent step the newly formed urea compound can be hydrolyzed with water, optionally containing a base or acid, to release its carbonyl group which can then be recycled into the process or separated off, for example as carbon dioxide or a ionic derivative thereof (such as hydrogen carbonate or carbonate salt). It should be noted that in embodiments of the present invention the cyclic urea unit of the newly formed urea compound is easier removed with a hydrolysis step than the urea of the starting cyclic urea compound. Also the newly formed cyclic urea compounds are in embodiments less susceptible to degradation during such hydrolysis than the starting cyclic urea compounds. Both these phenomena make the process of the present invention very favorable for such embodiments.

In a further preferred embodiment the released carbonyl group, i.e. often carbon dioxide, is continuously removed from the process which will enhance the process. The carbon dioxide can be removed for example by working in a suitable reactor unit comprising or connected to a section for actively removing CO2 by desorption, for instance by distillation, stripping or flashing, with or without a membrane.

In preferred embodiments the above subsequent step of hydrolyzing a potentially formed cyclic or non-cyclic urea to releasing carbon dioxide is performed by at least a step in which the materials are stripped. A person skilled in the art will know that such a stripping step is suitably done by having a sufficiently high flow of carrier gas and by ensuring good mixing and proper gas to liquid contact so that the maximum amount of carbon dioxide is removed from the system, in any way, the carbon dioxide should be so removed or isolated that it will not recombine with the amine compound with which it originally formed the cyclic urea, or any other amine compound.

In another preferred embodiment of the invention the amine compound or any urea compound formed from the reaction between the amine compound and the cyclic urea compound are recycled back into the process or separated off.

The process can be carried out in a batch reactor, possibly fed-batch operation, or in a continuously operating system such as in a cascade of continuous flow reactor.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

In such a scheme, the cyclic alkylene urea, amine compound and possibly water may be fed to the equipment as desired at a single point or at multiple points throughout the process equipment, which may include continuously stirred tank reactors, tubes, pipes, reactive distillation columns, reactive stripping units or combinations thereof.

In embodiments wherein a reactive distillation apparatus is used, the apparatus may comprise a reactive distillation column comprising at least one column internal, which column is on one side connected to a cooler unit and on the other side connected to a reboiler, and which apparatus is provided with an inlet for supplying the amine mixture, and one or more outlets for different distillate fractions. The process can be operated in batch-mode, fed batch mode, or continuously.

The process of the present invention typically depends on a number of reaction parameters such as the pressure in the column, the mass ratio of H2O to amine, the CO over amine fraction, the number and/or type of trays of the reactive distillation column, feeding point or points of the feed streams, the temperature of the cooler unit and/or reboiler, and the liquid residence time in the said column.

Preferably, the reactive distillation column comprises at least one column internal. Examples of such a column internal are a tray or packing. The number of trays of the reactive distillation column is also an important reaction parameter as these determine the effectiveness of the separation process of the reactants and products that takes place in the column, simultaneously with the reactions. Preferably, the number of trays in the column is at least 1, more preferably at least 2, and most preferably at least 5, and preferably at most 80, more preferably at most 60, most preferably at most 40. A skilled person further would understand that the size of the trays and the volume of the liquid, which each tray can contain, can vary and will also influence the reaction and/or separation effectiveness.

Desirably, the column will have trays, but any gas liquid contacting device might be suitable. Alternatively, suitable conventional packing, such as Raschig rings, Pall rings, saddles or structured packing of any kind might be used instead of trays. The different sections in the column might be equipped with different types of packing and/or trays.

The temperature of the cooler unit is lower than the reboiler temperature, and is chosen such that low-boiling products, such as the ethylene amine compound formed can leave the column, and that the reactants and high-boiling products remain in the system. The cooler unit can comprise just one cooler unit or may comprise a plurality of cooler sub-units, whereby each sub-unit has a specific temperature. A preferred embodiment of such a cooler unit comprises a first and a second cooler sub-unit. In a preferred embodiment a cooler unit is a condenser.

The person skilled in the art is capable of selecting the proper reactor and separation unit scheme by determining the overall yield, energy consumption and waste production.

In a most preferred embodiment a cyclic alkylene urea of EDA, DETA, TETA or TEPA, such as EU, UDETA, linear TETA mono- or diurea (UTETA or DUTETA) or linear TEPA mono or diurea (UTEPA or DUTEPA), is converted to EDA, DETA, linear TETA (L-TETA) or linear TEPA (L-TEPA) by employing DETA, TETA, TEPA, or larger ethylene amines.

The invention is illustrated by the below Examples

EXAMPLES

Example 1

Isothermal Batch Distillation

A batch distillation was performed by charging a distillation column with a mix of amines, urea-derivatives and water. The total mass of the starting mixture was 328 grams. The composition of the organic fraction of the starting mixture is summarized in Table 2. In addition the mixture contained 6 wt % of water at the start of the experiment. The starting mixture contained 0.97 moles of urea-derivatives.

The batch distillation column contained a packing of stainless steel wire mesh rings. A column length of 25 cm, corresponding to around 10 theoretical stages, was used during the experiments. Heat was supplied to the bottom section by an electrical heat plate with a metal jacket on top. During the course of the experiment the bottom temperature was kept within the temperature range of 190-230° C. and the pressure in the column was reduced in steps to yield three distillate fractions that have EDA, AEEA and TETA as main components.

The pressure levels were 95-97 mbar, 23-25 mbar and 4-8 mbar. The cooler in the top was cooled with cooling water so that a temperature between 35 and 97° C. was observed in the cooler, depending on the pressure level in the column. A cold trap was placed between the cooler and the vacuum pump that was cooled with a mix of ethanol and dry ice.

The distillation process was run for 10 hours. The top fractions collected during distillation and the initial and final bottom fractions were analyzed using a GC-FID (gas chromatography using a flame ionization detector). The product mixture before and after distillation is shown in Table 3.

Based on the GC-analysis data collected, it was concluded that all of the (U)EDA and (U)AEEA present in the starting mixture was successfully distilled and fully recovered as EDA and AEEA in one of the top fractions. This was surprising as originally a mix of EU and EDA and UAEEA and AEEA was present in the starting mixture.

Moreover, while before distillation the urea groups were distributed over light and heavy compounds, after distillation the urea groups were only present on the heavy compounds.

This shift in urea groups from the lighter compounds to the heavier compounds enabled the full recovery of EDA and AEEA and moreover has converted a mix of EU and EDA into a pure EDA product and a mix of UAEEA and AEEA into a pure AEEA product.

TABLE 2

Composition of the amine fraction at start of the experiment and as recovered.

| | Composition before distillation, mol fraction | Recovered in the distillate |
|---|---|---|
| (U)EDA | 16% | 100% |
| (U)AEEA | 8% | 100% |
| (U)TETA | 65% | 36% |
| (U)Amines larger than TETA | 10% | 0% |

TABLE 3

U distribution in the bottom of the column at before distillation and after distillation.

| U distribution | Before distillation (as mole % of U in mixture) | After distillation (as mole % of U in mixture) |
|---|---|---|
| Fraction U on lights[1] | 23% | 0% |
| Fraction U on heavies[2] | 77% | 100% |

[1]Lights defined as all compounds having less than 3 ethylene units.
[2]Heavies defined as all compounds having at least 3 ethylene units Example 2

Batch Distillation

A single-stage batch distillation was performed by charging a distillation vessel with a mix of amines and urea-derivatives. The total mass of the starting mixture was 221 grams. The composition of the starting mixture is summarized in Table 4.

The distillation vessel had a volume of 450 ml and was equipped with a condenser. Heat was supplied to the bottom section using an electrical heater. During the course of the experiment the bottom temperature was kept within the temperature range of 182-230° C. and the pressure in the column was kept between 150 mbar and 25 mbar. The cooler in the top was cooled with cooling water so that a temperature between 35 and 97° C. was observed in the cooler, depending on the pressure level in the column.

The distillation was run for 10 hours. The top fractions collected during distillation and the initial and final bottom fractions were analyzed using a GC-FID (gas chromatography using a flame ionization detector). The product mixture before and after distillation is shown in Table 4

TABLE 4

| Composition (mol) | Before distillation (mol) | Recovered in the distillate(s) (mol) |
|---|---|---|
| EDA | 0.33 | 0.95 |
| EU | 0.63 | 0.00 |
| AEEA | 0.02 | 0.34 |
| UAEEA | 0.35 | 0.00 |
| TETA | 0.30 | 0.00 |
| U1TETA | 0.31 | 0.00 |
| DUTETA | 0.00 | 0.00 |

During the distillation, 0.95 moles of EDA and 0.34 moles of AEEA were recovered from the starting mixture although at the start of the experiment this mixture contained only 0.33 moles of EDA and 0.02 moles of AEEA respectively.

The EDA and AEEA were recovered in different distillate fractions, hence, good separation of these compounds was achieved as well.

This clearly illustrates the shift of urea groups from the lighter compounds to the heavier compounds enabling the transfer of the cyclic urea unit of EU and UAEEA to the heavier amine compounds and simultaneous separation of the lighter ethylene amines without cyclic urea unit.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process to convert a cyclic alkylene urea into a corresponding alkylene amine, the process comprising reacting the cyclic alkylene urea with an amine compound chosen from the group of primary amines or secondary amines that have a higher boiling point than the alkylene amines formed during the process, wherein the process is a reactive separation process and the reaction mixture contains less than about 10 wt % of water on the basis of total weight of the reaction mixture, and wherein the process removes the carbonyl group of the cyclic alkylene urea to give the corresponding alkylene amine according to the following reaction scheme:

wherein:
each $R_3$ is alkylene or substituted alkylene;
$R_1$ and $R_2$ each independently are selected from the group consisting of hydrogen, an alkylene amine group of the formula $X-R_3-(NH-R_3-)_p$-, an alkoxy group of formula $X-R_3-(O-R_3-)_n$-, or a group combining such alkylene amine and alkoxy units;
X is a hydroxyl, an amine, a linear or branched C1-C20 hydroxyalkyl or C1-C20 aminoalkyl group;
n and p each independently are an integer from 0 to 20.

2. The process of claim 1 wherein the cyclic alkylene urea and the amine compound react in accordance with the reaction cyclic alkylene urea (UEA1)+alkylene amine (EA2)→alkylene amine (EA1)+cyclic alkylene urea (UEA2), wherein the alkylene amine EA2 has a higher boiling point than the alkylene amine EA1 formed in the process, and wherein the alkylene amine EA1 formed in the process is separated from the reaction mixture.

3. The process of claim 1 wherein X is a hydrogen atom, an aminoalkyl, an hydroxyalkyl, N-imidazolidinonealkyl or piperazinoalkyl group

4. The process of claim 1 wherein the amine compound is a compound that can bind the carbonyl group from the cyclic alkylene urea to give another linear or cyclic alkylene urea or linear or cyclic alkylene carbamate.

5. The process of claim 4 wherein the amine compound is an alkylene amine or an alkanol amine compound that is larger than the one derived from the starting cyclic alkylene urea after the conversion.

6. The process of claim 5 wherein the cyclic alkylene urea and the amine compound are chosen from the combinations of

| Cyclic alkylene urea | The amine compound |
|---|---|
| EU | DETA, TETA, TEPA, PEHA, AEEA, HE-DETA, HE-TETA, UTETA, UTEPA, UPEHA, HE-UTETA, |
| UDETA | TETA, TEPA, PEHA, AEEA, HE-DETA, HE-TETA, UTETA, UTEPA, UPEHA, HE-UTETA |
| UAEEA | TETA, TEPA, PEHA, HE-DETA, HE-TETA, UTETA, UTEPA, UPEHA, HE-UTETA, |
| UTETA, or DUTETA | TEPA, PEHA, HE-DETA, HE-TETA, UTETA, UTEPA, UPEHA, or HE-UTETA |
| HE-UDETA | TEPA, PEHA, HE-TETA, UTEPA, UPEHA, or HE-UTETA |
| UTEPA or DUTEPA | PEHA, HE-TETA, UTEPA, UPEHA, or HE-UTETA |
| UPEHA, DUPEHA or TUPEHA | UPEHA, or HE-UTETA | wherein EDA stands for ethylene diamine, DETA for diethylene triamine, TETA for triethylene tetramine, TEPA for tetraethylene pentamine, PEHA for pentaethylene hexamine, and, EU, UDETA, UTETA, UTEPA, and UPEHA for their respective monoureas, DUTETA, DUTEPA, and DUPEHA stand for the diureas of TETA, TEPA and PEHA, TUPEHA stands for the triurea of PEHA, AEEA for aminoethylethanolamine, UAEEA for the urea of aminoethylethanolamine), and HE stands for the presence of a hydroxyethyl group at one of the terminal amines of the mentioned ethylene amine.

7. The process of claim 1 wherein the reaction is done in less than about 7 wt % of water on total reaction mixture.

8. The process of claim 1 wherein the reaction is done at a pressure that is less than about 25 bar absolute pressure.

9. The process of claim 1 wherein the reaction is done at a pressure that is less than about 500 mbar absolute pressure.

10. The process of claim 1 wherein the reaction is done at a temperature of at least about 150° C.

11. The process of claim 1 wherein the amine compound is present during the process in a molar amount of from about 0.15 to about 25 equivalent based on the total molar amount of cyclic alkylene urea.

12. The process of claim 1 further comprising converting any urea compound formed from reaction between the amine compound and the cyclic urea compound to its corresponding amine while releasing its carbonyl group to provide carbon dioxide or an ionic derivative thereof.

13. The process of claim 12 further comprising recycling the carbon dioxide or ionic derivative thereof back into the process or separating the carbon dioxide or ionic derivative thereof.

14. The process of claim 1 further comprising recycling the amine compound or any urea compound formed from reaction between the amine compound and the cyclic urea compound back into the process or separating the amine compound or any urea compound formed from the reaction between the amine compound and the cyclic urea compound.

15. The process of claim 1 wherein n and/or p is 0.

16. The process of claim 1 wherein n and p each independently are an integer from 2 to 20.

17. The process of claim 1 wherein each $R_3$ is ethylene.

18. The process of claim 1 wherein $R_2$ is hydrogen, and wherein $R_1$ is not hydrogen.

19. The process of claim 1 wherein each $R_3$ is ethylene, wherein $R_2$ is hydrogen, and wherein $R_1$ is not hydrogen.

20. A process to convert a cyclic alkylene urea into a corresponding alkylene amine, the process comprising reacting the cyclic alkylene urea with a selected amine compound, wherein the process is a reactive separation process and the reaction mixture contains less than about 10 wt % of water on the basis of total weight of the reaction mixture, and wherein:

the cyclic alkylene urea is ethyleneurea (EU) and the selected amine compound is selected from the group consisting of diethylene triamine (DETA), triethylene tetramine (TETA), tetraethylene pentamine (TEPA), pentaethylene hexamine (PEHA), aminoethylethanolamine (AEEA), HE-DETA, HE-TETA, UTETA, UTEPA, UPEHA, HE-UTETA;

the cyclic alkylene urea is UDETA and the selected amine compound is selected from the group consisting of TETA, TEPA, PEHA, AEEA, HE-DETA, HE-TETA, UTETA, UTEPA, UPEHA, HE-UTETA;

the cyclic alkylene urea is the urea of aminoethylethanolamine (UAEEA) and the selected amine compound is selected from the group consisting of TETA, TEPA, PEHA, HE-DETA, HE-TETA, UTETA, UTEPA, UPEHA, HE-UTETA;

the cyclic alkylene urea is UTETA, or DUTETA and the selected amine compound is selected from the group consisting of TEPA, PEHA, HE-DETA, HE-TETA, UTETA, UTEPA, UPEHA, or HE-UTETA;

the cyclic alkylene urea is HE-UDETA and the selected amine compound is selected from the group consisting of TEPA, PEHA, HE-TETA, UTEPA, UPEHA, or HE-UTETA;

the cyclic alkylene urea is UTEPA or DUTEPA and the selected amine compound is selected from the group consisting of PEHA, HE-TETA, UTEPA, UPEHA, or HE-UTETA; or the cyclic alkylene urea is UPEHA, DUPEHA or the triurea of PEHA (TUPEHA) and the selected amine compound is selected from the group consisting of UPEHA, or HE-UTETA;

wherein UDETA, UTETA, UTEPA, and UPEHA each represent the monourea of the respective amine compound;

wherein DUTETA, DUTEPA, and DUPEHA each represent the diurea of the respective amine compound; and wherein HE- indicates the presence of a hydroxyethyl group at one of the terminal amines of the respective amine compound.

* * * * *